United States Patent [19]

Lautenschläger et al.

[11] Patent Number: 4,705,802
[45] Date of Patent: Nov. 10, 1987

[54] OMEGA-ARYL-ALKYLTHIENYL-COMPOUNDS AND PROCESS FOR THE TREATMENT OF CHRONICALLY INFLAMMATORY PROCESSES IN HUMANS

[75] Inventors: Hans-Heiner Lautenschläger; Michael J. Parnham; Sigurd Leyck, all of Pulheim; Johannes Winkelmann, Cologne; Axel Brekle, Bielefeld, all of Fed. Rep. of Germany

[73] Assignee: A. Nattermann & CIE GmbH, Cologne, Fed. Rep. of Germany

[21] Appl. No.: 705,671

[22] Filed: Feb. 26, 1985

[30] Foreign Application Priority Data

Mar. 1, 1984 [DE] Fed. Rep. of Germany ....... 3407510

[51] Int. Cl.$^4$ ..................... A61K 31/38; C07D 333/12
[52] U.S. Cl. ..................................... 514/438; 549/74; 549/75; 549/77; 549/79
[58] Field of Search ....................... 549/79, 74, 75, 77; 514/438

[56] References Cited

U.S. PATENT DOCUMENTS 3,960,893 6/1976 O'Mant ................................. 549/79
4,309,407 1/1982 Lautenschlager et al. ......... 424/275

FOREIGN PATENT DOCUMENTS 2103613 2/1983 United Kingdom .

OTHER PUBLICATIONS

Chemical Abstracts, C.A. 49, 13211 b–d, (1955).

Primary Examiner—Alan Siegel
Attorney, Agent, or Firm—Pearne, Gordon, McCoy & Granger

[57] ABSTRACT

The invention relates to new ω-aryl-alkylthienyl compounds having the Formula I

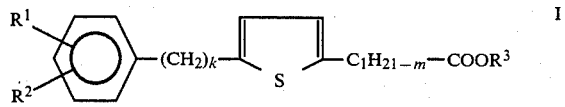

i.e. omega-aryl-alkyl thienyl alkanoic acids and, respectively, omega-aryl-alkyl thienyl alkenoic acids, the alkali metal salts of such acids and certain esters thereof. The invention further relates to processes for the treatment of chronically inflammatory processes in humans.

3 Claims, No Drawings

OMEGA-ARYL-ALKYLTHIENYL-COMPOUNDS AND PROCESS FOR THE TREATMENT OF CHRONICALLY INFLAMMATORY PROCESSES IN HUMANS

The invention relates to ω-aryl-alkylthienyl compounds having the formula I

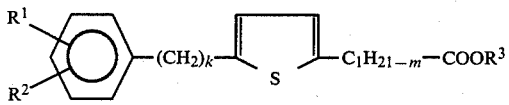

wherein k is an integer from 1 to 10, l is an integer from 2 to 10, m is zero or 2, $R^1$ and $R^2$ can be identical or different and independently of one another denote hydrogen, fluorine, chlorine, bromine or a $C_{1-4}$-alkyl, trifluoromethyl, hydroxyl, $C_{1-4}$-alkoxy, amino, $C_{1-4}$-alkylamino or di-$C_{1-4}$-alkylamino, $C_{1-4}$-acylamino or nitro group and $R^3$ denotes hydrogen, an alkaly metal ion, a straight-chain or branched alkyl group with 1 to 6 carbon atoms or a benzyl group. Excluded are those compounds of Formula I wherein l is 2 and m is zero.

Thus, the invention relates to omega-aryl-alkyl thienyl alkanoic acids of Formula I which in its —$CH_lH_{21-m}$-part may contain a double bond. These acids are the corresponding omega-aryl-alkyl thienyl alkenoic acids of Formula I wherein m always is the integer 2 and the —$C_lH_{21-m}$-part of the molekule always is an alkenylene group having the Formula —$C_{2-10}H_{2-18}$— and having an olefinically unsaturated double bond such as the —CH=CH—group with l being 2 and m being 2 or the —$CH_2$—CH=CH—$CH_2$—group with l being 4 and m being 2.

The ω-aryl-alkylthienylalkanoic(alkenoic) acids according to the invention and their derivatives exhibit a powerful antiinflammatory activity which is particularly suitable for the treatment of chronically inflammatory processes (for example diseases of the rheumatic type) and they therefore are used in the treatment of such processes and diseases in humans. It was found surprisingly that, in contrast to the usual non-steroid antiinflammatories, the action is not to be attributed to inhibition of the cyclooxygenase activity but to immuno-modulatory properties, i.e. properties which have both a controlled stimulating effect and an inhibiting effect on the immune system. Thus, the substances exhibit, for example, inhibition of the complement system, on the one hand, and a stimulating action on lymphocites, on the other hand; in an animal model of adjuvant arthritis, for example, stimulating or inhibiting effects can be observed both on prophylactic and on therepeutic administration, depending upon the circumstances.

The peculiarity of the compounds according to the invention lies in the selective inhibition of the lipoxygenase metabolism product leukotriene B4, whilst the enzyme cyclooxygenase remains uninfluenced.

The substances are furthermore used in the treatment of various ulcers in humans.

The compounds according to the invention include, for example, ω-[5-(phenylmethyl)-thien-b 2-yl]-propenoic acid, ω-[5-(phenylmethyl)-thien-2-yl]-butanoic acid, ω-[5-(phenylmethyl)-thien-2-yl]-but-3-enoic acid, ω-[5-(phenylmethyl)-thien-2-yl]-pentanoic acid, ω-[5-(phenylmethyl)-thien-2-yl]-pent-4-enoic acid, ω-[5-(phenylmethyl)-thien-2-yl]-hexanoic acid, ω-[5-(phenylmethyl)thien-2-yl]-hex-5-enoic acid, ω-[5-(2-phenylethyl)-thien-2-yl]-propenoic acid, ω-[5-(2-phenylethyl)-thien-2-yl]-butanoic acid, ω-[5-(2-phenylethyl)-thien-2-yl]-but-3-enoic acid, ω-[5-(2-phenylethyl)-thien-2-yl]-pentanoic acid, ω-[5-(2-phenylethyl)-thien-2-yl]-pent-4-enoic acid, ω-[5-(2-phenylethyl)-thien-2-yl]-hexanoic acid, ω-[5-(2-phenylethyl)-thien-2-yl]-hex-5-enoic acid, ω-[5-(3-phenylpropyl)-thien-2-yl]-propenoic acid, ω-[5-(3-phenylpropyl)-thien-2-yl]-butanoic acid, ω-[5-(3-phenylpropyl)-thien-2-yl]-but-3-enoic acid, ω-[5-(3-phenylpropyl)-thien-2-yl]-pentanoic acid, ω-[5-(3-phenylpropyl)-thien-2-yl]-pent-4-enoic acid, ω-[5-(3-phenylpropyl)-thien-2-yl]-hexanoic acid, ω-[5-(3-phenylpropyl)-thien-2-yl]-hex-5-enoic acid, ω-[5-(3-phenylpropyl)-thien-2-yl]-heptanoic acid, ω-[5-(3-phenylpropyl)-thien-2-yl]-hept-6-enoic acid, ω-[5-(3-phenylpropyl)-thien-2-yl]-octanoic acid, ω-[5-(3-phenylpropyl)-thien-2-yl]-oct-7-enoic acid, ω-[5-(3-phenylpropyl)-thien-2-yl]-nonanoic acid, ω-[5-(3-phenylpropyl)-thien-2-yl]-non-8-enoic acid, ω-[5-(3-phenylpropyl)-thien-2-yl]-decanoic acid, ω-[5-(3-phenylpropyl)-thien-2-yl]-dec-9-enoic acid, ω-[5-(3-phenylpropyl)-thien-2-yl]-undecanoic acid, ω-[5-(3-phenylpropyl)-thien-2-yl]-undec-10-enoic acid, ω-[5-(4-phenylbutyl)-thien-2-yl]-propenoic acid, ω-[5-(4-phenylbutyl)-thien-2-yl]-butanoic acid, ω-[5-(4-phenylbutyl)-thien-2-yl]-but-3-enoic acid, ω-[5-(4-phenylbutyl)-thien-2-yl]-pentanoic acid, ω-[5-(4-phenylbutyl)-thien-2-yl]-pent-4-enoic acid, ω-[5-(4-phenylbutyl)-thien-2-yl]-hexanoic acid, ω-[5-(4-phenylbutyl)-thien-2-yl]-hex-5-enoic acid, ω-[5-(5-phenylpentyl)-thien-2-yl]-propenoic acid, ω-[5-(5-phenylpentyl)-thien-2-yl]-propenoic acid, ω-[5-(5-phenylpentyl)-thien-2-yl]-butanoic acid, ω-[5-(5-phenylpentyl)-thien-2-yl]-but-3-enoic acid, ω-[5-(5-phenylpentyl)-thien-2-yl]-pentanoic acid, ω-[5-(5-phenylpentyl)-thien-2-yl]-pent-4-enoic acid, ω-[5-(5-phenylpentyl)-thien-2-yl]-hexanoic acid, ω-[5-(5-phenylpentyl)-thien-2-yl]-hex-5-enoic acid, ω-[5-(6-phenylhexyl)-thien-2-yl]-propenoic acid, ω-[5-(6-phenylhexyl)-thien-2-yl]-butanoic acid, ω-[5-(6-phenylhexyl)-thien-2-yl]-but-3-enoic acid, ω-[5-(6-phenylhexyl)-thien-2-yl]-pentanoic acid, ω-[5-(6-phenylhexyl)-thien-2-yl]-pent-4-enoic acid, ω-[5-(6-phenylhexyl)-thien-2-yl]-hexanoic acid, ω-[5-(6-phenylhexyl)-thien-2-yl]-hex-5-enoic acid, ω-[5-(7-phenylheptyl)-thien-2-yl]-propenoic acid, ω-[5-(7-phenylheptyl)-thien-2-yl]-butanoic acid, ω-[5-(7-phenylheptyl)-thien-2-yl]-but-3-enoic acid, ω-[5-(7-phenylheptyl)-thien-2-yl]-pentanoic acid, ω-[5-(7-phenylheptyl)-thien-2-yl]-pent-4-enoic acid, ω-[5-(7-phenylheptyl)-thien-2-yl]-hexanoic acid, ω-[5-(7-phenylheptyl)-thien-2-yl]-hex-5-enoic acid, ω-[5-(8-phenyloctyl)-thien-2-yl]-propenoic acid, ω-[5-(8-phenyloctyl)-thien-2-yl]-butanoic acid, ω-[5-(8-phenyloctyl)-thien-2-yl]-but-3-enoic acid, ω-[5-(8-phenyloctyl)-thien-2-yl]-pentanoic acid, ω-[5-(8-phenyloctyl)-thien-2-yl]-pent-4-enoic acid, ω-[5-(8-phenyloctyl)-thien-2-yl]-hexanoic acid and ω-[5-(8-phenyloctyl)-thien-2-yl]-hex-5-enoic acid.

The hydrogen atoms of the phenyl radicals in the abovementioned compounds can be substituted by suitable substituents (radicals $R^1$ and $R^2$ in formula I), for example: 5-{5-[3-(4-fluorophenyl)-propyl]-thien-2-yl}-pentanoic acid, 5-{5-[3-(4-chlorophenyl)-propyl]-thien-2-yl}-pentanoic acid, 5-{5-[3-(3,4-dichlorophenyl)-propyl]-thien-2-yl}-pentanoic acid, 5-{5-[3-(4-methylphenyl)-propyl]-thien-2-yl}-pentanoic acid, 5-{5-[3-(4-methoxyphenyl)-propyl]-thien-2-yl}-pentanoic acid, 5-{5-[3-(3,4-dimethoxyphenyl)-propyl]-thien-2-yl}-pentanoic acid, 5-{5-[3-(4-hydroxyphenyl)-propyl]-thien-2-yl}-pentanoic acid, 5-{5-[3-(3,4-dihydroxyphenyl)-propyl]-thien-2-yl}-pentanoic acid and 5-5-[3-(4-acetylaminophenyl)-propyl]-thien-2-yl-pentanoic acid.

Besides the acids mentioned, the corresponding derivatives are compounds according to the invention, such as, for example, sodium salts, potassium salts, methyl esters, ethyl esters, isopropyl esters and benzyl esters, for example, sodium 5-[5-(3-phenylpropyl)-thien-2-yl]-pentanoate, potassium 5-[5-(3-phenylpropyl)-thien-2-yl]-pentanoate, methyl 5-[5-(3-phenylpropyl)-thien-2-yl]-pentanoate, ethyl 5-[5-(3-phenylpropyl)-thien-2-yl]-pentanoate, isopropyl 5-[5-(3-phenylpropyl)-thien-2-yl]-pentanoate and benzyl 5-[5-(3-phenylpropyl)-thien-2-yl]-pentanoate.

The ω-aryl-alkylthienylakanoic(alkenoic) acids and their derivatives can be prepared by several processes. Thus, the saturated compounds can be synthesized by a process in which known ω-(2-thienyl)-alkanoic acid esters of the formula II

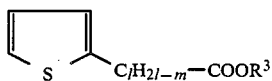

in which m is zero and l and $R^3$ have the meanings given in formula I, are reacted with ω-phenylalkanoic acid chlorides or anhydrides in the presence of Friedel-Crafts catalysts, such as, for example, aluminium chloride, tin tetrachloride, polyphosphoric acid and the like, in inert solvents, such as, for example, carbon disulphide, dichloroethane, trichloroethane, nitrobenzene and the like, to give 5-(ω-phenylalkanoyl)-thien-2-yl-alkanoic acid esters of the formula III

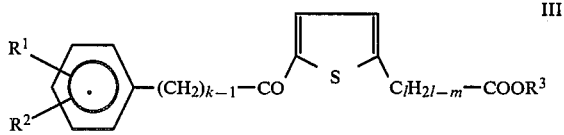

wherein m=0 and k, l, $R^1$, $R^2$ and $R^3$ have the meanings given in formula I, and the compounds III are reduced and hydrolysed with hydrazine, preferably in the presence of an alkali metal hydroxide and high-boiling solvents, such as, for example, diglycol or triglycol, at temperatures of 150°–220° C. to give the compounds I according to the invention where $R^3$=H. The compounds I where $R^3$=H can in turn be esterified or converted into the alkali metal salts by the customary processes.

A further possibility of synthesizing the compounds I comprises a process in which ω-phenylalkylthiophenes of the formula IV

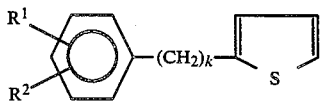

wherein k, $R^1$ and $R^2$ have the meanings given in formula I, are reacted with dicarboxylic acid dichlorides, dicarboxylic acid monoesters chlorides or dicarboxylic acid anhydrides in the presence of Friedel-Crafts catalysts, such as, for example, aluminium chloride, tin tetrachloride, polyphosphoric acid and the like, in inert solvents, such as, for example, carbon disulphide, dichloroethane, trichloroethane, nitrobenzene and the like, to give ω-oxo-ω-[5-(ω'-phenylalkyl)-thien-2-yl]-alkanoic acids or esters thereof, of the formula V

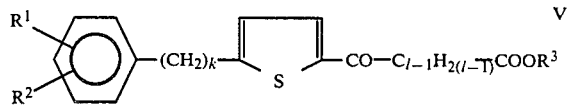

wherein k, l, $R^1$, $R^2$ and $R^3$ have the meanings given in formula I, and the compounds V are reduced and hydrolysed with hydrazine, preferably in the presence of an alkali metal hydroxide and high-boiling solvents, such as, for example, diglycol or triglycol, at temperatures of 150°–220° C. to give the compounds I according to the invention where $R^3$=H.

To prepare the ω-aryl-alkylthienylalkenoic acids, the arylalkylthiophenes IV are formylated with a Vilsmeyer complex, for example prepared from dimethylformamide/phosgene, dimethylformamide/phosphorus oxytrichloride or N-methylformanilide/phosphorus oxytrichloride,—if necessary with the addition of a solvent, such as dimethylformamide—to give the aldehydes of the formula VI

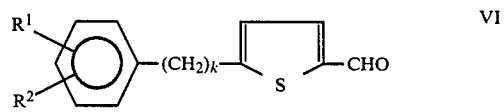

in which $R^1$, $R^2$ and k have the meanings given in formula I, and the resulting aldehydes are in turn condensed with malonic acid or malonic acid monoesters in a suitable medium, such as, for example, pyridine or pyridine/piperidine, to give the alkenoic acids I or esters thereof where l=2 and m=2.

The alkenoic acids and alkenoic acid esters I where l>2 and m=2 are likewise obtained from the aldehydes VI by reacting these with ω-hydroxycarbonylalkyl- or ω-alkoxycarbonylalkyl-phosphonium salts or -phosphonic acid esters in the presence of strong bases, such as, for example, sodium hydride, sodium amide, sodium methylsulphinylmethanide, n-butyl-lithium or potassium tert.-butylate, in inert solvents, such as, for example, dimethylformamide or dimethylsulphoxide.

The present invention also relates to pharmaceutical products containing compounds of the formula I. The pharmaceutical products according to the invention are those for enternal, such as oral or rectal, and parenteral administration, which contain the pharmaceutical active compounds by themselves or together with a customary pharmaceutically usable excipient. The pharmaceutical formulation of the active compound is advantageously in the form of individual doses which are matched to the desired administration, such as, for example, tablets, coated tablets, capsules, suppositories, granules, solutions, emulsions or suspensions. The dosage of the compounds is usually between 0.1–500 mg per dose, preferably between 1–150 mg per dose, and can be administered once or several times, preferably two or three times, daily.

The preparation of the compounds according to the invention is illustrated in more detail by the following examples. The melting points given were measured with a Büchi 510 melting point determination apparatus and are uncorrected. The IR spectra were recorded with a Perkin Elmer 257 apparatus and the mass spectral with a MAT-311A apparatus.

EXAMPLE 1

5-[5-(3-Phenylpropyl)-thien-2-yl]-valeric acid.

(a) Methyl 5-[5-(1-oxo-3-phenylpropyl)-thien-2-yl]-valerate.

40 g of powdered aluminium chloride are added to 200 ml of 1,2-dichloroethane and 50 g of methyl 5-(2-thienyl)-valerate are added dropwise, while cooling with ice. 44.3 g of 3-phenylpropionyl chloride are then added such that the temperature does not rise above 20° C. the mixture is stirred at room temperature for 14 hours and poured onto ice and a little concentrated hydrochloric acid is added to dissolve precipitated aluminium chloride. The organic phase is separated off, the aqueous phase is extracted twice with dichloroethane, the organic extracts are combined, washed with 5% strength sodium bicarbonate solution and water and dried over sodium sulphate and the solvent is evaporated off in vacuo. The residue is purified by column chromatography (silica gel/chloroform).

Yield: 42 g of oil
IR (film): 1740, 1655 cm$^{-1}$ (b) 5-[5-(3-Phenylpropyl)-thien-2-yl]-valeric acid.

14 g of methyl 5-[5-(1-oxo-3-phenylpropyl)-thien-2-yl]-valerate, 100 ml of triethylene glycol, 7.8 g of potassium hydroxide and 4.8 g of hydrazine hydrate are mixed, the mixture is heated under reflux for 2 hours and a mixture of hydrazine and water is then slowly distilled off, until the temperature in the reaction mixture is 195° C. When the evolution of nitrogen has ended, the solution is cooled, diluted with 100 ml of water, acidified and extracted with ether. The ether extract is washed with water and dried over sodium sulphate and the solvent is stripped off. The residue is purified by column chromatography (silica gel/chloroform).

Yield: 2.8 g of oil
IR (film): 1710 cm$^{-1}$
MS [m/e]: 302 (M$^+$, 100%), 215 (56%), 198 (72%) and 111 (41%)

EXAMPLE 2

Sodium 5-[5-(3-phenylpropyl)-thien-2-yl]-valerate.

3 g of 5-[5-(3-phenylpropyl)-thien-2-yl]-valerate are mixed with 50% strength ethanol and the equivalent amount of sodium hydroxide, the mixture is stirred for 1 hour and the solvent is stripped off in vacuo. The residue is powdered.

Yield: quantitative
IR (in KBr): 1565 cm$^{-1}$

EXAMPLE 3

5-[5-(5-Phenylpentyl)-thien-2-yl]-valeric acid.

(a) Methyl 5-[5-(1-oxo-5-phenylpentyl)-thien-2-yl]-valerate.

This compound is prepared analogously to Example 1a from: 100 ml of 1,2-dichloroethane, 21 g of aluminium chloride, 26 g of methyl 5-(2-thienyl)-valerate and 27 g of 5-phenylvaleryl chloride.

Yield: 31 g of oil
IR (film): 1740, 1660 cm$^{-1}$ (b) 5-[5-(5-Phenylpentyl)-thien-2-yl]-valeric acid.

This compound is prepared analogously to Example 1b from: 15 g of methyl 5-[5-(1-oxo-5-phenylpentyl)-thien-2-yl]-valerate, 7.6 g of potassium hydroxide, 100 ml of triethylene glycol and 5 g of hydrazine hydrate.

Yield: 7.4 g of melting point 33° C.
IR (in KBr): 1712 cm$^{-1}$
MS [m/e]: 330 (M$^+$, 100%), 243 (86%), 197 (93%) and 91 (40%)

EXAMPLE 4

Sodium 5-[5-(5-phenylpentyl)-thien-2-yl]-valerate.

This compound is prepared analogously to Example 2.

IR (in KBr): 1565 cm$^{-1}$

EXAMPLE 5

5-[5-(6-Phenylhexyl)-thien-2-yl]-valeric acid.

(a) Methyl 5-[5-(1-oxo-6-phenylhexyl)-thien-2-yl]-valerate.

This compound is prepared analogously to Example 1a from: 100 ml of 1,2-dichloroethane, 24.2 g of aluminium chloride, 30.6 g of methyl 5-(2-thienyl)-valerate and 34.0 g of 5-phenylvaleryl chloride.

Yield: 40.1 g (b) 5-[5-(6-Phenylhexyl)-thien-2-yl]-valeric acid.

This compound is prepared analogously to Example 1b from: 22.8 g of methyl 5-[5-(1-oxo-6-phenylhexyl)-thien-2-yl]-valerate, 11.1 g of potassium hydroxide, 250 ml of triethylene glycol and 7.0 g of hydrazine hydrate.

Yield: 14.5 g of melting point 54° C.
IR (in KBr): 1705 cm$^{-1}$
MS [m/e]: 344 (M$^+$, 83%), 257 (68%), 197 (100%) and 91 (72%)

EXAMPLE 6

Sodium 5-[5-(6-phenylhexyl)-thien-2-yl]-valerate.

This compound is prepared analogously to Example 2.

IR (in KBr): 1565 cm$^{-1}$

EXAMPLE 7

6-[5-(Benzyl)-thien-2-yl]-hex-5-enoic acid.

(a) 5-Benzyl-thiophene-2-aldehyde.

139 g of 2-benzylthiophene are dissolved in 204 ml of dimethylformamide, and 143 g of phosphorus oxytrichloride are added dropwise to the solution, with cooling (temperature not above 20° C.). The mixture is warmed at 80° C. for 3 hours and cooled, ice is added, the pH is brought to 6 with 20% strength sodium hydroxide solution and the mixture is extracted with chloroform. The chloroform solution is washed with water, dried over sodium sulphate and concentrated. The residue is purified by column chromatography (silica gel/chloroform).

Yield: 22 g of oil
IR (film): 2800, 1660 cm$^{-1}$ (b) 6-[5-(Benzyl)-thien-2-yl]-hex-5-enoic acid.

6.4 g of sodium hydride (=8 g of 80% strength mineral oil suspension) are washed with n-pentane and dissolved in 180 ml of dry dimethylsulphoxide at 80° C., hydrogen being evolved. A solution of 59.5 g of 4-hydroxycarbonylbutyltriphenylphosphonium bromide in 180 ml of dimethylsulphoxide is added dropwise to this solution, under nitrogen and while cooling with ice. The mixture is stirred for 10 minutes and a solution of 22 g of 5-benzyl-thiophene-2-aldehyde is added dropwise, during which the temperature does not rise above 20° C., and the mixture is stirred for a further hour. Thereafter, the reaction mixture is poured onto ice, acidified and extracted with ether. The ether phase is washed with water, dried over sodium sulphate and concentrated in vacuo. The residue is purified by column chromatography (silica gel/hexane/ethyl acetate).

Yield: 20 g of oil, cis/trans mixture
IR (film): 1708 cm$^{-1}$

EXAMPLE 8

6-[5-(4-Chlorobenzyl)-thien-2-yl]-hex-5-enoic acid.

(a) 5-(4-Chlorobenzyl)-thiophene-2-aldehyde.

This compound is prepared analogously to Example 7a from: 62.3 g of 2-(4-chlorobenzyl)-thiophene, 76 ml of dimethylformamide and 55 g of phosphorus oxytrichloride.

Yield: 19.3 g of oil
IR (film): 2800, 1665 cm$^{-1}$ (b) 6-[5-(4-Chlorobenzyl)-thien-2-yl]-hex-5-enoic acid.

This compound is prepared analogously to Example 7b from: 6.3 g of sodium hydride ($\hat{=}$7.8 g of 80% strength mineral oil suspension) in 180 ml of dimethylsulphoxide, 57.9 g of 4-hydroxycarbonylbutyl-triphenylphosphonium bromide in 180 ml of dimethylsulphoxide and 25.0 g of 5-(4-chlorobenzyl)-thiophene-2-aldehyde in 20 ml of dimethylsulphoxide.

Yield: 11 g of oil, cis/trans mixture
IR (film): 1710 cm$^{-1}$

In principle, the cis/trans mixtures of the ω-aryl-alkylthienylalkenoic acids described in Examples 7 and 8 can also be separated by column chromatography (for example on silica gel); however, to simplify the separation, it is advantageous first to convert the acids into the esters.

EXAMPLE 9

Ethyl 5-[5-(3-phenylpropyl)-thien-2-yl]-valerate.

3 g of 5-[5-(3-phenylpropyl)-thien-2-yl]-valeric acid are dissolved in 10 ml of ethanol and the solution is saturated with HCl gas. The solution is stirred at room temperature for 24 hours and concentrated in vacuo. Purification by column chromatography (silica gel/hexane/ethyl acetate).

Yield: 2.95 g of oil
IR (film): 1735 cm$^{-1}$

What we claim is:

1. An ω-aryl-alkylthienyl compound having the formula I

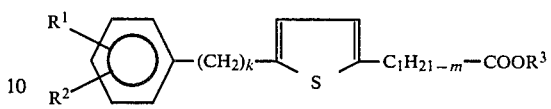

wherein k is an integer from 3 to 10, l is an integer from 4 to 10, m is zero or 2, $R^1$ is a member selected from the group consisting of hydrogen, fluorine, chlorine, bromine, $C_{1-4}$-alkyl, trifluoromethyl, hydroxyl, $C_{1-4}$-alkoxy, amino, $C_{1-4}$-alkylamino, di-$C_{1-4}$-alkylamino, $C_{1-4}$-acylamino and nitro, $R^2$ is a member selected from the group consisting of hydrogen, fluorine, chlorine, bromine, $C_{1-4}$-alkyl, trifluorometyl, hydroxyl, $C_{1-4}$-alkoxy, amino, $C_{1-4}$-alkylamino, di-$C_{1-4}$-alkylamino, $C_{1-4}$-acylamino and nitro, and $R^3$ is a member selected from the group consisting of hydrogen, the alkali metal ions, the straight-chain and the branched alkyl groups with 1 to 6 carbon atoms and the benzyl group.

2. ω-Aryl-alkylthienyl compounds according to claim 1 wherein k is a integer from 3 to 10, l is an integer from 4 to 10, m is zero or 2, $R^1$ is a member selected from the group consisting of hydrogen, fluorine, chlorine, methyl, trifluoromethyl, hydroxyl, methoxy, amino and acetylamino, $R^2$ is a member selected from the group consisting of hydrogen, fluorine, chlorine, methyl, trifluoromethyl, hydroxyl, methoxy, amino and acetylamino, and $R^3$ is a member selected from the group consisting of hydrogen, the alkali metal ions and the alkyl groups methyl, ethyl and isopropyl.

3. Process for the treatment of chronically inflammatory processes in humans comprising administering to the human suffering from a chronically inflammatory process a compound according to claim 1 or 2 in a dosage ranging from 0.1 to 500 mg per dose once or several times daily.

* * * * *